United States Patent [19]

Miyakawa et al.

[11] Patent Number: 5,319,209

[45] Date of Patent: Jun. 7, 1994

[54] METHOD FOR MEASUREMENT OF INTRACELLULAR ION CONCENTRATION USING FLUORESCENCE PROBE DYES

[75] Inventors: Atsuo Miyakawa; Kiyoshi Kamiya; Masahiko Hirano, all of Hamamatsu, Japan

[73] Assignee: Hammamatsu Photonics K.K., Hamamatsu, Japan

[21] Appl. No.: 979,703

[22] Filed: Nov. 19, 1992

[30] Foreign Application Priority Data

Nov. 20, 1991 [JP] Japan .................................. 3-304832

[51] Int. Cl.⁵ ...................... G01N 21/64; G01N 21/78
[52] U.S. Cl. ............................. 250/459.1; 250/461.2
[58] Field of Search ...................... 250/372, 373, 461.2, 250/459.1, 458.1, 461.1

[56] References Cited

U.S. PATENT DOCUMENTS

| | | | |
|---|---|---|---|
| 4,603,209 | 7/1986 | Tsien et al. | 548/236 |
| 4,849,362 | 7/1989 | DeMarinis et al. | 436/63 |
| 4,900,934 | 2/1990 | Peeters et al. | 250/461.2 |
| 5,149,972 | 9/1992 | Fay et al. | 250/461.1 |

FOREIGN PATENT DOCUMENTS 339582 11/1989 European Pat. Off. .......... 250/458.1
3-120446 5/1991 Japan ................................ 250/458.1

OTHER PUBLICATIONS

Grynkiewicz et al., "A New Generation of $Ca^{2+}$ Indicators with Greatly Improved Fluorescence Properties", Jour. Biological Chem., vol. 260, No. 6, Mar. 1985, pp. 3440–3450.

Primary Examiner—Constantine Hannaher
Assistant Examiner—Edward J. Glick
Attorney, Agent, or Firm—Cushman Darby & Cushman

[57] ABSTRACT

A fluorescence probe dye is introduced into a cell, and excitation beams at three defferent wavelengths are irradiated to the cell to measure intensities of the fluorescence generated by the excitation beams, corresponding to the three wavelengths. Then, an equilibrium reaction equation for concentrations of the fluorescence probe dye, protein, free ions and their complexes in the cell, and a relationship equation between the fluorescence probe dye, protein, free ions and their complexes are used as simultaneous equations to give concentrations of the respective components. This process can correct interactions among various components of the cell due to bonding among them and a correct ion concentration can be determined.

15 Claims, 2 Drawing Sheets

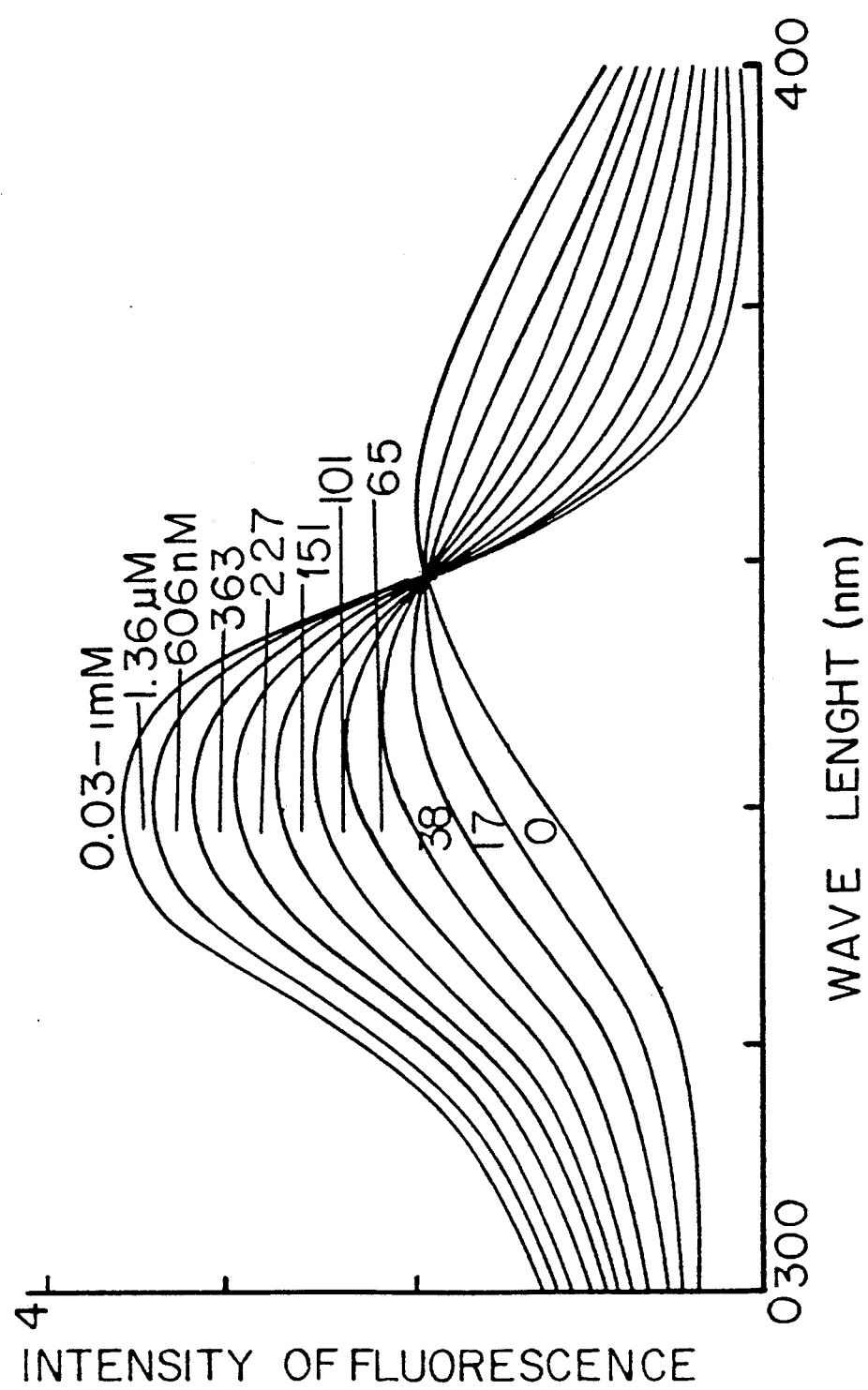

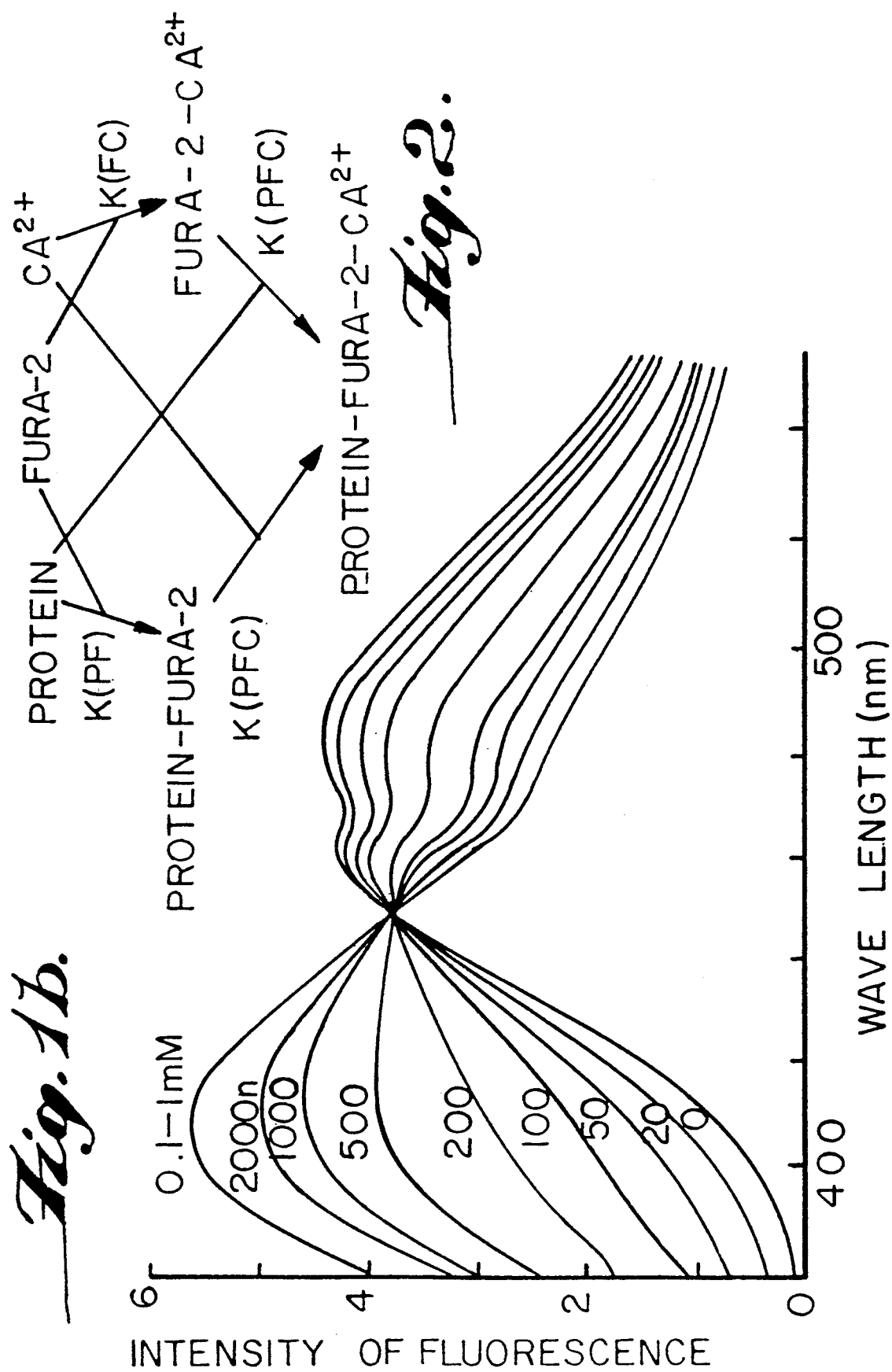

METHOD FOR MEASUREMENT OF INTRACELLULAR ION CONCENTRATION USING FLUORESCENCE PROBE DYES

BACKGROUND OF THE INVENTION

1. Field of the Invention

This invention relates to a method for measuring distributions and changes of concentrations of ions, in a cell, which contribute to controlling of functions, etc. of the cell.

2. Related Background Art

In quantifying concentrations of free ions, such as calcium ions, etc., which are present in a live cell, fluorescence probe dyes, such as Fura-2, Indo-1, etc., are used. The methods of synthesis and characteristics of these dyes are described in "The Journal of Biological Chemistry, Vol. 260, No. 6, pp. 3340-3450 (1985)" and "Biophysical Journal, Vol. 54, pp. 1089-1104 (1988)". These probe dyes have a characteristic that they bond with and dissociate from certain ions to have variable fluorescence characteristics. Due to this characteristic, a probe dye is applied into a cell, and an intensity of fluorescence generated by an excitation beam is measured, whereby an ion concentration in the cell can be measured.

The measurement based on excitation beams at only one wavelength and fluorescence of only one wavelength cannot give accurate measured values when distribution of a probe dye in the cell is not uniform. In addition there is a possibility that changes of a fluorescence intensity, such as attenuation of fluorescence, etc., which are independent of an ion concentration are measured together.

To make up for this disadvantage a method has been employed in which a fluorescence probe dye having an isosbestic point is used to measure either fluorescence intensities corresponding to excitation beams at two different wavelengths, or intensities of fluorescence at two wavelengths generated by an excitation beam of one wavelength, and the ratio of the fluorescence at the two wavelengths is determined.

FIGS. 1A and 1B show examples of the prior art, demonstrating excitation spectra and emission spectra of a fluorescence probe dye used in the above-described method. FIG. 1A shows excitation spectra of Fura-2 for measuring a concentration of calcium ions in samples, and the figures above the curves depicting the spectra indicate calcium ion concentrations in samples. As shown, a characteristic of Fura-2 is that it bonds with calcium ions in a cell to increase the fluorescence intensity in response to an excitation beam of 340 nm wavelength. Conversely, its fluorescence intensity is decreased by an excitation beam of 380 nm wavelength. Another characteristic of Fura-2 is that an intensity of the fluorescence generated by an excitation beam of 360 nm wavelength is independent of concentrations of calcium ions. In the case where Fura-2 is used, a calcium ion concentration is given based on a fluorescence intensity ratio between, e.g., 340 nm and 380 nm, or 340 nm and 360 nm, and on a calibration curve prepared beforehand. The calibration curve for converting a value of the fluorescence intensity ratio into an absolute value of a concentration can be obtained by preparing a dye containing calcium ions of a known concentration, introducing a fluorescence probe dye thereinto and measuring a fluorescence intensity ratio.

FIG. 1B is a fluorescence spectra of Indo-1 and shows spectra at respective wavelengths of fluorescence generated when a cell is irradiated with an excitation beam of 355 nm wavelength. Indo-1 has an isosbestic point at around a fluorescence wavelength of 440 nm, as does Fura-2. Accordingly, in the same way as the above-described case using Fura-2, a calcium ion concentration in the cell can be given based on a fluorescence intensity ratio between two wavelengths of the fluorescence generated by the irradiation of an excitation beam of one wavelength.

Measuring devices for use in the above-described measuring methods using fluorescence probe dyes are spectrofluorometers, microphotometers combining fluorescence microscopes and photomultipliers, image analyzers combining fluorescence microscopes and television cameras, etc.

The above-described methods are elaborated in "A. Miyakawa et al., Bunseki Kagaku, Vol. 38, No. 11, pp. 842-649 (1989)", and "A. Miyakawa, Photomedical and Photobiology, Vol. 13, pp. 15-18 (1981)".

In the above-described dual wavelength fluorescence measuring method, an error deriving from a non-homogenous concentration of a probe dye introduced into a cell can be corrected by calculating a fluorescence intensity ratio.

The above-described method is usable in cases where a probe dye is reactive only with certain ions, but it is considered that in a cell the probe dye bonds also with protein, membrane components, etc. which are present there in high concentrations. Accordingly fluorescence spectra of the probe dye, and a chelating constant thereof with ions adversely change. Then a problem with the dual wavelength fluorescence measuring method is that an error resulting from such interactions between the dye and components other than ions cannot be corrected, and an accurate ion concentration cannot be given.

SUMMARY OF THE INVENTION

An object of this invention is to provide a method for measuring an ion concentration in a cell, which has successfully solved the above-described problem.

Substances which generate fluorescence in a cell when a fluorescence probe dye is introduced into the cell and the cell is irradiated with an excitation beam include the probe dye, complexes of the probe dye and free ions to be measured (hereinafter called ions), complexes of the probe dye and various proteins (hereinafter called protein), and complexes of the probe dye, the ions and the protein. These fluorescent substances are present in the cell in a chemical equilibrium state with the ions and protein. That is, among the substances present in the cell, six kinds of substances are involved in the fluorescence measurement. In the fluorescence measurement concentrations of these substances are unknown values. To determine these six unknown values it is necessary to acquire six relationship equations which are independent of one another.

Three of the six relationship equations can be obtained based on the following chemical equilibrium conditions.

$$K_{FI} = X_F X_I / X_{FI}$$

$$K_{PF} = X_P X_F / X_{PF}$$

$$K_{PFI} = X_P X_{FI} / X_{PFI} \text{ (or, } K_{PFI} = X_{PF} X_I / X_{PFI})$$

wherein
$X_F$: a concentration of a fluorescence probe dye,
$X_I$: a concentration of free ions
$X_P$: a concentration of protein
$X_{FI}$: a concentration of fluorescence probe dye-free ions complexes
$X_{PF}$: a concentration of protein-fluorescence probe dye complexes
$X_{PFI}$: a concentration of protein-fluorescence probe dye-free ions complexes
$K_{FI}$: an equilibrium constant between fluorescence probe dye and free ions complexes
$K_{PF}$: an equilibrium constant between protein and fluorescence probe dye
$K_{PFI}$: an equilibrium constant between protein and fluorescence probe dry-free ions complexes The remaining three relationship equations can be acquired as follows by measuring fluorescence intensities corresponding to excitation beams at three different wavelengths, or intensities of three wavelength fluorescence corresponding to an excitation beam of one wavelength.

$$I_{\lambda 1}=I_{\lambda 1,F}X_F+I_{\lambda 1,PF}X_{PF}+I_{\lambda 1,FI}X_{FI}+I_{\lambda 1,PFI}X_{PFI}$$

$$I_{\lambda 2}=I_{\lambda 2,F}X_F+I_{\lambda 2,PF}X_{PF}+I_{\lambda 2,FI}X_{FI}+I_{\lambda 2,PFI}X_{PFI}$$

$$I_{\lambda 3}=I_{\lambda 3,F}X_F+I_{\lambda 3,PF}X_{PF}+I_{\lambda 3,FI}X_{FI}+I_{\lambda 3,PFI}X_{PFI}$$

wherein
$I_{\lambda i}$: a measured fluorescence intensity for an excitation beam of wavelength $\lambda_i$
$I_{\lambda i,F}$: a fluorescence intensity coefficient of a fluorescence probe dye for an excitation beam of wavelength $\lambda_i$
$I_{\lambda i,PF}$: a fluorescence intensity coefficient of protein-fluorescence probe dye complexes for an excitation beam of wavelength $\lambda_i$
$I_{\lambda i,FI}$: a fluorescence intensity coefficient of a fluorescence probe dye-free ion complexes for an excitation beam at wavelength $\lambda_i$
$I_{\lambda i,PFI}$: a fluorescence intensity coefficient of protein-fluorescence probe dye-free ions complexes for excitation beam of a wavelength $\lambda_i$
i: 1, 2, 3 or
$I_{\lambda 1}$: a measured fluorescence intensity at a wavelength $\lambda_i$
$I_{\lambda i,F}$: a fluorescence intensity coefficient of a fluorescence probe dye at a wavelength $\lambda_i$
$I_{\lambda i,PF}$: a fluorescence intensity coefficient of protein-fluorescence probe dye complexes at a wavelength $\lambda_i$
$I_{\lambda i,FI}$: a fluorescence intensity coefficient of fluorescence probe dye-free ion complexes at wavelength $\lambda_i$
$I_{\lambda i,PFI}$: a fluorescence intensity coefficient of protein-fluorescence probe dye-free ions complexes at a wavelength $\lambda_i$
i: 1, 2, 3

As described above, six independent relationship equations are acquired for the six unknown values, whereby a concentration of free ions in the cell can be determined.

This invention provides a method for measuring an ion concentration in a cell using a fluorescence probe dye introduced into a cell. Excitation beams are irradiated to the cell to generate fluorescence, and, based on an intensity of the fluorescence, a free ion concentration in the cell is determined. The method comprises a first step of measuring intensities of fluorescence generated by irradiating excitation beams at three wavelengths to the cell corresponding to the respective wavelengths; and a second step of using the following types of equations as simultaneous equations to give concentrations of the fluorescence probe dye, protein, free ions and their respective complexes which are present in the cell, where one type of equations are equilibrium reaction equations of concentrations of the fluorescence probe dye, protein, free ions and their respective complexes which are present in the cell, and the other type of equations are relationship equations expressing relationships between concentrations of the fluorescence probe dyes, the protein, the free ions and their respective complexes and the intensities of the fluorescence.

Where the free ions to be measured are $Ca^{2+}$, the fluorescence probe dye is Fura-2.

Where the free ions to be measured are $Na^+$, the fluorescence probe dye is Sodium-binding benzofuran isophthalate.

Where the free ions to be measured are $K^+$, the fluorescence probe dye is Potassium-binding benzofuran isophthalate.

Where the free ions to be measured are $H^+$, the fluorescence probe dye is 2',7'-bis-(2-carboxyethyl)-(5-(and-6)-carboxyfluoresoein).

Alternatively, where the free ions to be measured are $H^+$, the fluorescence probe dye is carboxy-seminaphthorhodafluor-6.

Where the free ions to be measured are $Mg^{2+}$, the fluorescence probe dye is Mag-Fura-2.

Furthermore this invention provides a method for measuring an ion concentration in a cell where a fluorescence probe agent is loaded into a cell, and excitation beams are irradiated to the cell to generate fluorescence. Based on intensity of the fluorescence, a free ion concentration in the cell is determined. The method comprises a first step of measuring intensities of fluorescence at three wavelength generated by irradiating an excitation beam at one wavelength to the cell corresponding to the respective wavelengths; and a second step of using the following types of equations as simultaneous equations to give concentrations of the fluorescence probe dye, protein, free ions and their respective complexes which are present in the cell, where one type of equations are equilibrium reaction equations on concentrations of the fluorescence probe dye, protein, free ions and their respective complexes which are present in the cell, and the other type of equations are relationship equations expressing relationships between concentrations of the fluorescence probe dyes, the protein, the free ions and their respective complexes and the intensities of the fluorescence.

Furthermore, where the free ions to be measured are $Ca^{2+}$, the fluorescence probe dye is Indo-1.

Where the free ions to be measured are $Na^+$, the fluorescence probe dye is FCryp-2.

Where the free ions to be measured are $H^+$, the fluorescence probe dye is Carboxyseminaphthorhodafluor-1.

Where the free ions to be measured are H+, the fluorescence probe dye is Carboxyseminaphthorhodafluor-2.

Alternatively, where the free ions to be measured are H+, the fluorescence probe dye is Carboxyseminaphthorhodafluor-6.

Alternatively, where the free ions to be measured are H+, the fluorescence probe dye is Carboxyseminaphthorhodafluor-X.

Where the free ions to be measured are $Mg^{2+}$, the fluorescence probe dye is Mag-indo-1.

BRIEF DESCRIPTION OF THE DRAWINGS

FIG. 1A is a graph showing relationships among concentrations of calcium ions in a solution, excitation wavelength and generated fluorescence intensities.

FIG. 2B is a graph showing relationships among concentration of calcium ions in a solution, emission wavelengths and fluorescence intensities.

FIG. 2 is a view showing interactions of substances in a cell with Fura-2 introduced into the cell.

DETAILED DESCRIPTION OF THE INVENTION

Examples of this invention will be explained below by means of cases where the method for measuring one wavelength fluorescence corresponding to three wavelength excitation beams.

To prepare samples, Fura-2 was used as a probe dye, and Fura-2 was introduced into a cell by a known method.

FIG. 2 shows a view approximating interactions between Fura-2 and calcium ions ($Ca^{2+}$) or protein in the cell. FIG. 2 shows the measurement of $Ca^{2+}$ using Fura-2, but the same approximation can be made for the measurement of $Ca^{2+}$ dyes, e.g., Indo-1. In the cell, Fura-2 bonds with $Ca^{2+}$ at a equilibrium constant K(FC) and also with protein at a equilibrium constant K(PF). Furthermore, the three components, Fura-2, $Ca^{2+}$ and protein, bond with one another at a equilibrium constant K(PFC) or K'(PFC). Accordingly the following equations (1) to (4) are based these three bonding components:

$$K(FC)=[F][C]/[FC] \quad (1)$$

$$K(PF)=[P][F]/[PF] \quad (2)$$

$$K(PFC)=[P][FC]/[PFC] \quad (3)$$

$$K'(PFC)=[PF][C]/[PFC] \quad (4)$$

In the above-described equations, F represents Fura-2, C, $Ca^{2+}$; P, protein; and [ ], a concentration of a component.

Excitation beams were irradiated to the above-described sample, and spectra of the generated fluorescence were measured. The excitation beams had three wavelengths of 340 nm, 360 nm and 380 nm. In the cell were present four components, free Fura-2, Fura-2-calcium ion complexes, Fura-2-protein complexes and Fura-2-calcium ion-protein complexes. The intensity of the fluorescence corresponding to each wavelength is a sum of intensities of the fluorescence of the respective components. Accordingly, the following equations (5) to (7) determine the intensity at each respective wavelength:

$$I_{340}=[F]I(F)_{340}+[PF]I(PF)_{340}+[FC]I(FC)_{340}+[PFC]I(PFC)_{340} \quad (5)$$

$$I_{360}=[F]I(F)_{360}+[PF]I(PF)_{360}+[FC]I(FC)_{360}+[PFC]I(PFC)_{360} \quad (6)$$

$$I_{380}=[F]I(F)_{380}+[PF]I(PF)_{380}+[FC]I(FC)_{380}+[PFC]I(PFC)_{380} \quad (7)$$

In these equations, known values are an equilibrium constant K(FC) between Fura-2 and $Ca^{2+}$, an equilibrium constant K(PF) between Fura-2 and protein, an equilibrium constant K(PFC) between Fura-2-calcium ion complexes and protein, a equilibrium constant K'(PFC) between Fura-2-protein complexes and calcium ions, fluorescence intensities I(F) of free Fura-2 at 340 nm, 360 nm and 380 nm wavelengths of the excitation beams, a fluorescence intensity I(FC) of Fura-2-calcium ion complexes, a fluorescence intensity I(PF) of Fura-2-protein complexes, and a fluorescence intensity I(PFC) of Fura-2-calcium ions-protein complexes.

Thus a concentration of free $Ca^{2+}$ in the cell can be determined by measuring the intensities I340, I360, I380 of a cell with Fura-2 introduced into the cell, where the measurement of the intensities is conducted with excitation beams of 340 nm, 360 nm and 380 nm wavelengths. In addition to concentrations of total Fura-2 loaded into a cell, concentrations of calcium ions and protein interacting with the fluorescence probe dye can be determined.

In the above-described measuring method, Fura-2 was used as a fluorescence probe dyes, but other probe dye, e.g., Indo-1, may be used. Where Indo-1 is used, it is preferable because of its fluorescence characteristics to measure intensities of three wavelength fluorescence corresponding to an excitation beam of one wavelength. In this case, a beam of a wavelength (355 nm) which most excites Indo-1 is irradiated to a cell prepared in the same way as in the measurement of an intensity of one wavelength fluorescence corresponding to excitation beams at three wavelengths, and intensities of the generated fluorescence at three wavelengths are measured. Subsequently the same measuring steps as in the measurement of one wavelength fluorescence corresponding to excitation beams at three wavelengths are followed. An equilibrium reaction equation, and a relationship equation among concentrations of the respective components and fluorescence intensities are used as simultaneous equations whereby unknown concentrations of the components in the cell can be accurately determined.

The fluorescence probe dye and the excitation wavelength are not limited to the values used in the examples and may be varied depending on fluorescence characteristics of dyes with the object of this invention fully achieved.

What is claimed is:

1. A method for measuring intracellular ion concentration by use of a fluorescence probe dye, in which a fluorescence probe dye is introduced into a cell, and a concentration of free ions in the cell is measured, based on intensities of fluorescence generated by irradiating the cell with excitation beams, the method comprising:

the first step of irradiating excitation beams at three different wavelengths to the cell, and measuring intensities of the fluorescence generated by the excitation beams, corresponding to the respective three different wavelengths; and the second step of solving simultaneous equations of (1) equilibrium constant equations of the fluorescence probe dye, protein, free ions to be measured and their complexes in the cell, and (2) relationship equations between the intensities of the fluorescence generated by the excitation beams at the respective wavelengths, and the concentration of fluorescence probe dye, protein, free ions to be measured and their complexes, wherein the equations are $$K_{FI} = X_F X_I / X_{FI}$$

$$K_{PF} = X_P X_F / X_{PF}$$

$$K_{PFI} = X_P X_{FI} / X_{PFI} \text{ (or, } K_{PFI} = X_{PF} X_I / X_{PFI})$$

$$I_{\lambda 1} = I_{\lambda 1, F} X_F + I_{\lambda 1, PF} X_{PF} + I_{\lambda 1, FI} X_{FI} + I_{\lambda 1, PFI} X_{PFI}$$

$$I_{\lambda 2} = I_{\lambda 2, F} X_F + I_{\lambda 2, PF} X_{PF} + I_{\lambda 2, FI} X_{FI} + I_{\lambda 2, PFI} X_{PFI}$$

$$I_{\lambda 3} = I_{\lambda 3, F} X_F + I_{\lambda 3, PF} X_{PF} + I_{\lambda 3, FI} X_{FI} + I_{\lambda 3, PFI} X_{PFI}$$

wherein
$X_F$: a concentration of a fluorescence probe dye,
$X_I$: a concentration of free ions
$X_P$: a concentration of protein
$X_{FI}$: a concentration of fluorescence probe dye-free ions complexes
$X_{PF}$: a concentration of protein-fluorescence probe dye complexes
$X_{PFI}$: a concentration of protein-fluorescence probe dye-free ions complexes
$X_{FI}$: an equilibrium constant between fluorescence probe dye and free ions complexes
$K_{PF}$: an equilibrium constant between protein and fluorescence probe dye
$K_{PFI}$: an equilibrium constant among protein, fluorescence probe dye and free ions
$I_{\lambda i}$: a measured fluorescence intensity for an excitation beam of wavelength $\lambda_i$
$I_{\lambda i, F}$: a fluorescence intensity coefficient of a fluorescence probe dye for an excitation beam of wavelength $\lambda_i$
$I_{\lambda i, PF}$: a fluorescence intensity coefficient of protein-fluorescence probe dye complexes for an excitation beam of wavelength $\lambda_i$
$I_{\lambda i, FI}$: a fluorescence intensity coefficient of fluorescence probe dye-free ion complexes for an excitation beam at wavelength $\lambda_i$
$I_{\lambda i, PFI}$: a fluorescence intensity coefficient of protein-fluorescence probe dye-free ions complexes for excitation beam of a wavelength $\lambda_i$
i: 1, 2, 3.

2. A method for measurement of an intracellular ion concentration in a cell by use of a fluorescence probe dye according to claim 1, wherein
the free ions to be measured are $Ca^{2+}$, and
the fluorescence probe dye is Fura-2.

3. A method for measurement of an intracellular ion concentration in a cell by use of a fluorescence probe dye according to claim 1, wherein
the free ions to be measured are $Na^+$, and
the fluorescence probe dye is Sodium-binding benzofuran isophthalate.

4. A method for measurement of an intracellular ion concentration in a cell by use of a fluorescence probe dye according to claim 1, wherein
the free ions to be measured are $K^+$, and
the fluorescence probe dye is Potassium-binding benzofuran isophthalate.

5. A method for measurement of an intracellular ion concentration in a cell by use of a fluorescence probe dye according to claim 1, wherein
the free ions to be measured are $H^+$, and
the fluorescence probe dye is 2',7'-bis-(2-carboxyethyl)-(5-(and-6)-carboxyfluoresoein).

6. A method for measurement of an intracellular ion concentration in a cell by use of a fluorescence probe dye according to claim 1, wherein
the free ions to be measured are $H^+$, and
the fluorescence probe dye is carboxyseminaphthorhodafluor-6.

7. A method for measurement of an intracellular ion concentration in a cell by use of a fluorescence probe dye according to claim 1, wherein
the free ions to be measured are $Mg^{2+}$, and
the fluorescence probe dye is Mag-Fura-2.

8. A method for measuring intracellular ion concentration in a cell by use of a fluorescence probe dye, in which a fluorescence probe dye introduced into a cell, and a concentration of free ions in the cell is measured, based on intensities of fluorescence generated by irradiating the cell with an excitation beam, the method comprising:

the first step or irradiating an excitation beam of one wavelength to the cell, and measuring intensities of the fluorescence of three wavelengths generated by the excitation beam; and
the second step of solving simultaneous equations of (1) equilibrium constant equations of the fluorescence probe dye, protein, free ions to be measured and their complexes in the cell, and (2) relationship equations between the intensities of the fluorescence of the three wavelengths generated from the excitation by the excitation beam, and the concentrations of fluorescence probe dye, protein, free ions to be measured and their complexes, wherein the equations are $$K_{FI} = X_F X_I / X_{FI}$$

$$K_{PF} = X_P X_F / X_{PF}$$

$$K_{PFI} = X_P X_{FI} / X_{PFI} \text{ (or, } K_{PFI} = X_{PF} X_I / X_{PFI})$$

$$I_{\lambda 1} = I_{80}$$
$$1, F \cdot X_F + I_{\lambda 1, PF} X_{PF} + I_{\lambda 1, FI} X_{FI} + I_{\lambda 1, PFI} X_{PFI}$$

$$I_{\lambda 2} = I_{\lambda 2, F} X_F + I_{\lambda 2, PF} X_{PF} + I_{\lambda 2, FI} X_{FI} + I_{\lambda 2, PFI} X_{PFI}$$

$$I_{\lambda 3} = I_{\lambda 3, F} X_F + I_{\lambda 3, PF} X_{PF} + I_{\lambda 3, FI} X_{FI} + I_{\lambda 3, PFI} X_{PFI}$$

wherein
$X_F$: a concentration of a fluorescence probe dye,
$X_I$: a concentration of free ions
$X_P$: a concentration of protein
$X_{FI}$: a concentration of fluorescence probe dye-free ions complexes
$X_{PF}$: a concentration of protein-fluorescence probe dye complexes $X_{PFT}$: a concentration of protein-fluorescence probe dye-free ions complexes $K_{FT}$: an equilibrium constant between fluorescence probe dye and free ions $K_{PF}$: an equilibrium constant between protein and fluorescence probe dye $K_{PFT}$: an equilibrium constant among protein, fluorescence probe dye and free ions $I_{\lambda i}$: a measured fluorescence intensity at a wavelength $\lambda_i$ $I_{\lambda i,F}$: a fluorescence intensity coefficient of a fluorescence probe dye at a wavelength $\lambda_i$ $I_{\lambda i,PF}$: a fluorescence intensity coefficient of protein-fluorescence probe dye complexes at a wavelength $\lambda_i$ $I_{\lambda i,FT}$: a fluorescence intensity coefficient of fluorescence probe dye-free ion complexes at wavelength $\lambda_i$ $I_{\lambda i,PFT}$: a fluorescence intensity coefficient of protein-fluorescence probe dye-free ions complexes at a wavelength $\lambda_i$ i: 1, 2, 3.

9. A method for measurement of an intracellular ion concentration in a cell by use of a fluorescence probe dye according to claim 8, wherein the free ions to be measured are $Ca^{2+}$, and the fluorescence probe dye is Indo-1.

10. A method for measuring of an intracellular ion concentration in a cell by use of a fluorescence probe dye according to claim 8, wherein the free ions to be measured are $Na^+$, and the fluorescence probe dye is FCryp-2.

11. A method for measurement of an intracellular ion concentration in a cell by use of a fluorescence probe dye according to claim 8, wherein the free ions to be measured are $H^+$, and the fluorescence probe dye is Carboxyseminaphthorhodafluor-1.

12. A method for measurement of an intracellular ion concentration in a cell by use of a fluorescence probe dye according to claim 8, wherein the free ions to be measured are $H^+$, and the fluorescence probe dye is Carboxyseminaphthorhodafluor-2.

13. A method for measurement of an intracellular ion concentration in a cell by use of a fluorescence probe dye according to claim 8, wherein the free ions to be measured are $H^+$, and the fluorescence probe dye is Carboxyseminaphthorhodafluor-6.

14. A method for measurement of an intracellular ion concentration in a cell by use of a fluorescence probe dye according to claim 8, wherein the free ions to be measured are $H^+$, and the fluorescence probe dye is Carboxyseminaphthorhodafluor-X.

15. A method for measurement of an intracellular ion concentration in a cell by use of a fluorescence probe dye according to claim 8, wherein the free ions to be measured are $Mg^{2+}$, and the fluorescence probe dye is Mag-indo-1.

* * * * *